US010588564B2

(12) United States Patent
Moein et al.

(10) Patent No.: US 10,588,564 B2
(45) Date of Patent: Mar. 17, 2020

(54) METHOD AND KIT FOR DIAGNOSING AND TREATING NEOPLASTIC TISSUE

(71) Applicant: Moein Health, LLC, San Diego, CA (US)

(72) Inventors: Sudabeh Moein, San Diego, CA (US); Frederick J. Zustak, San Diego, CA (US)

(*) Notice: Subject to any disclaimer, the term of this patent is extended or adjusted under 35 U.S.C. 154(b) by 0 days.

(21) Appl. No.: 15/971,822

(22) Filed: May 4, 2018

(65) Prior Publication Data

US 2018/0249943 A1 Sep. 6, 2018

Related U.S. Application Data

(63) Continuation-in-part of application No. 15/052,819, filed on Feb. 24, 2016, now abandoned, and a
(Continued)

(51) Int. Cl.
*A61B 10/00* (2006.01)
*A61B 10/02* (2006.01)
(Continued)

(52) U.S. Cl.
CPC .......... *A61B 5/4331* (2013.01); *A61B 1/0638* (2013.01); *A61B 1/303* (2013.01); *A61B 1/32* (2013.01); *A61B 5/0071* (2013.01); *A61B 5/0084* (2013.01); *A61B 10/0096* (2013.01); *A61B 10/0291* (2013.01); *A61B 10/04* (2013.01); *A61B 42/10* (2016.02); *A61B 46/20* (2016.02); *A61B 50/30* (2016.02); *A61B 50/33* (2016.02); *A61F 17/00* (2013.01); *A61K 31/19* (2013.01); *A61K 31/4166* (2013.01); *A61K 49/006* (2013.01); *A61K 49/0043* (2013.01); *A61M 31/005* (2013.01); *A61B 2050/0065* (2016.02); *A61B 2050/3008* (2016.02);
(Continued)

(58) Field of Classification Search
CPC ... A61B 5/4331; A61B 5/0071; A61B 5/0085; A61B 42/10; A61B 46/20; A61B 50/30; A61B 50/33; A61B 1/0638; A61B 1/303; A61B 1/32; A61B 10/0096; A61B 10/0291; A61B 10/04; A61B 2050/0065; A61B 2050/3008; A61B 2560/0443; A61F 17/00; A61F 13/38; A61K 31/19; A61K 31/4166; A61K 49/0043; A61K 49/006; A61M 31/005; A61M 2210/1475
USPC .............. 600/108, 473–480; 604/1, 107, 167
See application file for complete search history.

(56) References Cited

U.S. PATENT DOCUMENTS 5,476,664 A 12/1995 Robinson et al.
6,761,900 B2 7/2004 Shudo et al.
(Continued)

OTHER PUBLICATIONS

Gaspar et al., Colposcopia de luz antinica, validez para deteccion de lesiones vervicales producidas por virus de papiloma humano, Revista de Enfermedades del Tracto Genital Inferior, Dec. 2013, pp. 12-17, vol. 7, No. 1.
Giesler et al., Short-Term Efficacy of Trichloroacetic Acid in the Treatment of Cervical Intraepithelial Neoplasia, Obstetrics & Gynecology, Feb. 2016, pp. 353-359, vol. 127, No. 2, Wolters Kluwer Health, Inc.

*Primary Examiner* — Pedro Philogene

(57) ABSTRACT

The disclosure concerns a medical kit arranged with componentry for fluorescein sodium (FNa)-based diagnosis and trichloroacetic acid (TCA)-based treatment of neoplastic tissue, and related methods for utilizing aspects of the medical kit.

21 Claims, 7 Drawing Sheets

Related U.S. Application Data continuation-in-part of application No. 14/870,642, filed on Sep. 30, 2015, now abandoned.

(60) Provisional application No. 62/182,606, filed on Jun. 21, 2015, provisional application No. 61/120,356, filed on Feb. 24, 2015, provisional application No. 62/057,584, filed on Sep. 30, 2014.

(51) Int. Cl.

| | | |
|---|---|---|
| *A61B 10/04* | (2006.01) | |
| *A61B 1/06* | (2006.01) | |
| *A61B 1/303* | (2006.01) | |
| *A61B 5/00* | (2006.01) | |
| *A61B 50/33* | (2016.01) | |
| *A61M 31/00* | (2006.01) | |
| *A61B 42/10* | (2016.01) | |
| *A61B 46/20* | (2016.01) | |
| *A61K 49/00* | (2006.01) | |
| *A61B 1/32* | (2006.01) | |
| *A61F 17/00* | (2006.01) | |
| *A61B 50/30* | (2016.01) | |
| *A61K 31/19* | (2006.01) | |
| *A61K 31/4166* | (2006.01) | |
| *A61F 13/38* | (2006.01) | |
| *A61B 50/00* | (2016.01) | |

(52) U.S. Cl.
CPC ....... *A61B 2560/0443* (2013.01); *A61F 13/38* (2013.01); *A61M 2210/1475* (2013.01)

(56) References Cited

U.S. PATENT DOCUMENTS

| | | |
|---|---|---|
| 8,877,788 B2 | 11/2014 | Farber |
| 2003/0087960 A1* | 5/2003 | Burstein ............... A61K 31/19 514/557 |
| 2004/0002125 A1* | 1/2004 | Gombrich .......... G01N 15/1456 435/7.23 |
| 2004/0023415 A1* | 2/2004 | Sokolov ............... A61B 5/0059 436/518 |
| 2004/0207625 A1* | 10/2004 | Griffin ................ A61B 5/0059 345/440 |
| 2006/0204474 A1 | 9/2006 | Coroneo |
| 2011/0165077 A1* | 7/2011 | Qian .................. A61K 49/0023 424/9.1 |
| 2011/0212090 A1* | 9/2011 | Pedersen ............ A61K 39/0011 424/133.1 |
| 2012/0325704 A1* | 12/2012 | Kerns .................... A61B 50/33 206/370 |
| 2013/0045522 A1 | 2/2013 | Charles et al. |
| 2014/0039322 A1 | 2/2014 | Trujillo et al. |
| 2014/0170693 A1* | 6/2014 | Ince ..................... C12N 5/0682 435/29 |
| 2016/0256523 A1 | 9/2016 | Rapraeger et al. |
| 2016/0271132 A1 | 9/2016 | Hampson et al. |
| 2016/0279083 A1 | 9/2016 | Moein et al. |
| 2016/0370285 A1 | 12/2016 | Jang et al. |
| 2017/0165320 A1 | 6/2017 | Vadlamudi et al. |
| 2017/0202982 A1 | 7/2017 | Mohs et al. |
| 2017/0332910 A1 | 11/2017 | Friedman et al. |
| 2017/0333347 A1 | 11/2017 | Lin et al. |

\* cited by examiner providing a medical kit comprising: a speculum, a light source, and a plurality of pre-filled containers, wherein the plurality of pre-filled containers comprises at least:
a first containing saline solution,
a second containing acetic acid, and
a third containing fluorescein sodium

↓ diagnosing the cervical intraepithelial neoplasia

↓ treating the cervical tissue indicating intraepithelial neoplasia based on the findings

↓ repeating the diagnosing and treating until there are no findings of neoplastic tissue

FIG.2

```
┌─ inserting the speculum into a patient's vagina to expose the entire cervix of the patient
│
├─ rinsing the patient's cervix with the saline solution contained
│  in the first of the pre-filled containers to remove discharge and detritus
│
├─ using the light source and colposcope:
│  visually identifying abnormal cervical vasculature
│  with green light from the light source
│
├─ applying the acetic acid contained
│  in the second of the pre-filled containers
│  to the patient's cervix for staining abnormal tissue acetowhite
│
├─ applying aqueous iodine solution to the patient's cervix
│  for staining normal tissue brown
│
├─ using the colposcope:
│  visualizing the patient's cervix and
│  identifying brown staining of benign tissue in conjunction
│  with acetowhite staining of abnormal tissue, and recording findings
│
├─ rinsing the patient's cervix with the saline solution
│
├─ applying the fluorescein sodium contained in the third of the
│  pre-filled containers to the patient's cervix
│
├─ visualizing fluorescent green staining of malignant and premalignant tissue
│  using blue light of the light source, and recoding findings
│
├─ performing one or more cervical biopsies and endocervical curettage if desired
│  to compare with cytological results or proceeding with treatment based on the findings
│
└─ if biopsies are performed and bleeding occurs at biopsy sites,
   obtaining hemostasis by applying silver nitrate to affected areas
```

*FIG.3*

METHOD AND KIT FOR DIAGNOSING AND TREATING NEOPLASTIC TISSUE

CROSS-REFERENCE TO RELATED APPLICATIONS

This application is a continuation in part (CIP) of commonly owned U.S. patent application Ser. No. 15/052,819, filed Feb. 24, 2016, which claims benefit of priority with U.S. Prov. Ser. No. 62/182,606, filed Jun. 21, 2015, and further claims benefit of priority with U.S. Prov. Ser. No. 62/120,356, filed Feb. 24, 2015; and is a CIP of commonly owned U.S. patent application Ser. No. 14/870,642, filed Sep. 30, 2015, which claims benefit of priority with U.S. Prov. Ser. No. 62/057,584, filed Sep. 30, 2014;

the entire contents of each of which are hereby incorporated by reference.

BACKGROUND

Field of the Invention

This invention relates to medical kits for treating neoplastic tissue; and more particularly, to such medical kits arranged with componentry for fluorescein sodium (FNa)-based diagnosis and trichloroacetic acid (TCA)-based treatment of neoplastic tissue.

Description of the Related Art

Cervical cancer was the third most commonly diagnosed cancer in women in 2012, with an estimated 529,828 new cases worldwide and a 52% mortality rate globally. Complex diagnostic procedures and analysis laboratories are impracticable in many remote locales.

The current method for diagnosing cervical cancer is colposcopy in which acetic acid is used as a staining agent to visualize abnormal tissue. Meanwhile, current management of patients with cervical intraepithelial neoplasia (CIN) includes the following treatments: Loop Electrical Excision Procedure (LEEP), Cold Knife Conization (CKC), cryosurgery, laser ablation, or hysterectomy. These procedures lead to partial destruction of the cervix. At the very least, the destruction will render the patient's future colposcopies unsatisfactory because the physician will be unable to clearly visualize the squamocolumnar junction due to scarring. A more serious side effect is cervical incompetence, which poses the most impact to women of reproductive age who are still planning to have children. This destruction is of most concern for patients with recurrent disease because additional treatments on a shorter cervix are more challenging surgically. Such drastic treatment is recommended only when colposcopic acetic acid visualization indicates cervical neoplasia. However, such indication is generally only seen when the lesions are in an advanced stage when using acetic acid visualization, when it would have been preferable to diagnose and treat lower-grade lesions much earlier.

Despite its long history as a diagnostic procedure, colposcopy continues to have varying success. In conjunction with acetic acid, the sensitivity of colposcopy to distinguish normal from abnormal tissue is relatively high. The accuracy, however, to distinguish low-grade lesions from high-grade lesions and cancer remains low. Additionally, a substantial proportion of high-grade lesions may fail to be identified at colposcopy. In a most recent post hoc analysis of more than 47,000 women, approximately 20% additional CIN 2 or worse and CIN 3 or worse was identified in women who did not have a visible lesion on colposcopy. Therefore, the treatment of CIN I may be just as important as treating CIN II or III.

The low sensitivity to distinguish low-grade lesions from high-grade lesions and cancer suggests that a substantial number of women may be over-treated. Equally importantly, a substantial proportion of high-grade lesions may fail to be identified at colposcopy.

Additionally, inter-observer variable rates of 52.4% and 51.0% have also been described in previous studies.

SUMMARY

The disclosure concerns a medical kit arranged with componentry for fluorescein sodium (FNa) solution-based diagnosis and trichloroacetic acid (TCA)-based treatment of neoplastic tissue, and related methods for utilizing aspects of the medical kit.

In one aspect, a medical kit for use in the diagnosis and treatment of tissue exhibiting intraepithelial neoplasia (neoplastic tissue) is disclosed.

In a preferred embodiment, the medical kit generally includes at least: a speculum; a light source; and a plurality of pre-filled containers, wherein the plurality of pre-filled containers comprises at least: a first containing normal saline solution, a second containing acetic acid, a third containing Lugol's aqueous iodine solution, a fourth containing normal saline solution, a fifth containing fluorescein sodium solution and a sixth containing normal saline solution.

The light source can be configurable in each of three states, including: a first state wherein the light source in the first state is configured to emit polychromatic light for visualizing tissue, a second state wherein the light source in the second state is configured to emit green light for visualizing a pattern of vascularization in the tissue, and a third state wherein the light source in the third state is configured to emit blue light for visualizing staining of abnormal tissue. The polychromatic light may comprise light in the spectral range of 350 nm to 700 nm. The green light may consist essentially of light in the spectral range of 495 nm to 625 nm. The blue light may consist essentially of light in the spectral range of 350 nm to 495 nm. In some embodiments, the three states are each individually achieved via an electronic circuit configured to selectively power one of three light emitting diodes, wherein each of the light emitting diodes is configured to emit one of said polychromatic, green and blue lights. In other embodiments, the light source may comprise a chemiluminescent light source. The light source can be configured to couple with the speculum. Alternatively, the light source can be embodied within the speculum.

The first of the plurality of pre-filled containers containing normal saline solution may comprise a pre-filled pipette containing between 10.0 mL and 100.0 mL of the normal saline solution.

The second of the plurality of pre-filled containers containing acetic acid may comprise a pre-filled pipette containing between 10.0 mL and 100.0 mL of 4% acetic acid solution.

The third of the plurality of pre-filled containers containing between 10.0 mL and 100.0 mL of aqueous iodine solution, said aqueous iodine solution comprising less than 2% concentration of iodine.

The fourth of the plurality of the pre-filled containers containing normal saline solution may comprise a pre-filled pipette containing between 10.0 mL and 100.0 mL of the normal saline solution.

The fifth of the plurality of pre-filled containers containing fluorescein sodium solution (FNa) may comprise a pre-filled pipette containing between 10.0 mL and 100.0 mL of fluorescein sodium solution.

The sixth of the plurality of the pre-filled containers containing normal saline solution may comprise a pre-filled pipette containing between 10.0 mL and 100 mL of the normal saline solution.

The medical kit may further include trichloroacetic acid (TCA). The trichloroacetic acid may comprise 1.0% to 99.0% trichloroacetic acid in aqueous solution.

The medical kit may further comprise one or more silver nitrate sticks.

The medical kit may further comprise an amount of basic ferric sulfate solution.

The medical kit may further comprise: gloves, lubricating jelly, cotton swabs, one amber-colored glass jar, gauze, an under-buttock drape, a disposable Keyes biopsy punch or any combination of one or a plurality thereof.

In another aspect, a method for using the medical kit described herein for diagnosis and treatment of tissue exhibiting intraepithelial neoplasia (neoplastic tissue) is disclosed.

In a preferred embodiment, the method includes at least: providing a medical kit comprising: a speculum, a light source, and a plurality of pre-filled containers, wherein the plurality of pre-filled containers comprises at least: a first containing normal saline solution, a second containing acetic acid, a third containing Lugol's aqueous iodine solution, a fourth containing normal saline solution, a fifth containing fluorescein sodium solution and a sixth containing normal saline solution; diagnosing the cervical intraepithelial neoplasia, and treating the cervical tissue indicating intraepithelial neoplasia.

In a preferred embodiment, the diagnosing step may comprise: inserting the speculum into a patient's vagina to expose the entire cervix of the patient; rinsing the patient's cervix with the normal saline solution contained in the first of the pre-filled containers to remove discharge and detritus; using the light source and colposcope: visually identifying abnormal cervical vasculature with green light from the light source; applying the acetic acid contained in the second of the pre-filled containers to the patient's cervix for staining abnormal tissue acetowhite; applying the aqueous iodine solution contained in the third of the pre-filled containers to the patient's cervix for staining normal tissue brown; using the colposcope: visualizing the patient's cervix and identifying brown staining of benign tissue in conjunction with acetowhite staining of abnormal tissue, and recording findings; rinsing the patient's cervix with the normal saline solution contained in the fourth of the pre-filled containers; applying the fluorescein sodium solution contained in the fifth of the pre-filled containers to the patient's cervix; waiting at least 60 seconds before visualizing fluorescent green staining of malignant and premalignant tissue using blue light on the light source, and recording findings; rinsing the patient's cervix with the normal saline solution contained in the sixth of the pre-filled containers; performing one or more cervical biopsies and endocervical curettage if desired to compare with cytological results or proceeding with treatment based on the findings; and if biopsies are performed and bleeding occurs at biopsy sites, obtaining hemostasis by applying silver nitrate to affected areas.

In a preferred embodiment, the treating step may comprise: applying trichloro acetic acid solution to an entirety of the patient's cervix; using a first swab: collecting an amount of the applied trichloroacetic acid and further spreading the trichloroacetic acid solution to the squamocolumnar junction and the endocervix; using a second swab: removing excess trichloroacetic acid solution to prevent incidental chemical cauterization of the vaginal wall; removing the speculum from the vagina; and repeating the diagnosing and treating until there are no findings of neoplastic tissue.

BRIEF DESCRIPTION OF THE DRAWINGS

FIG. 2 shows a method for diagnosing and treating neoplastic tissue using the kit as-illustrated in FIG. 1;

FIG. 3 further illustrates additional steps for diagnosing neoplastic tissue using the medical kit as-illustrated in FIG. 1;

DETAILED DESCRIPTION OF THE PREFERRED EMBODIMENTS

Figure 1:
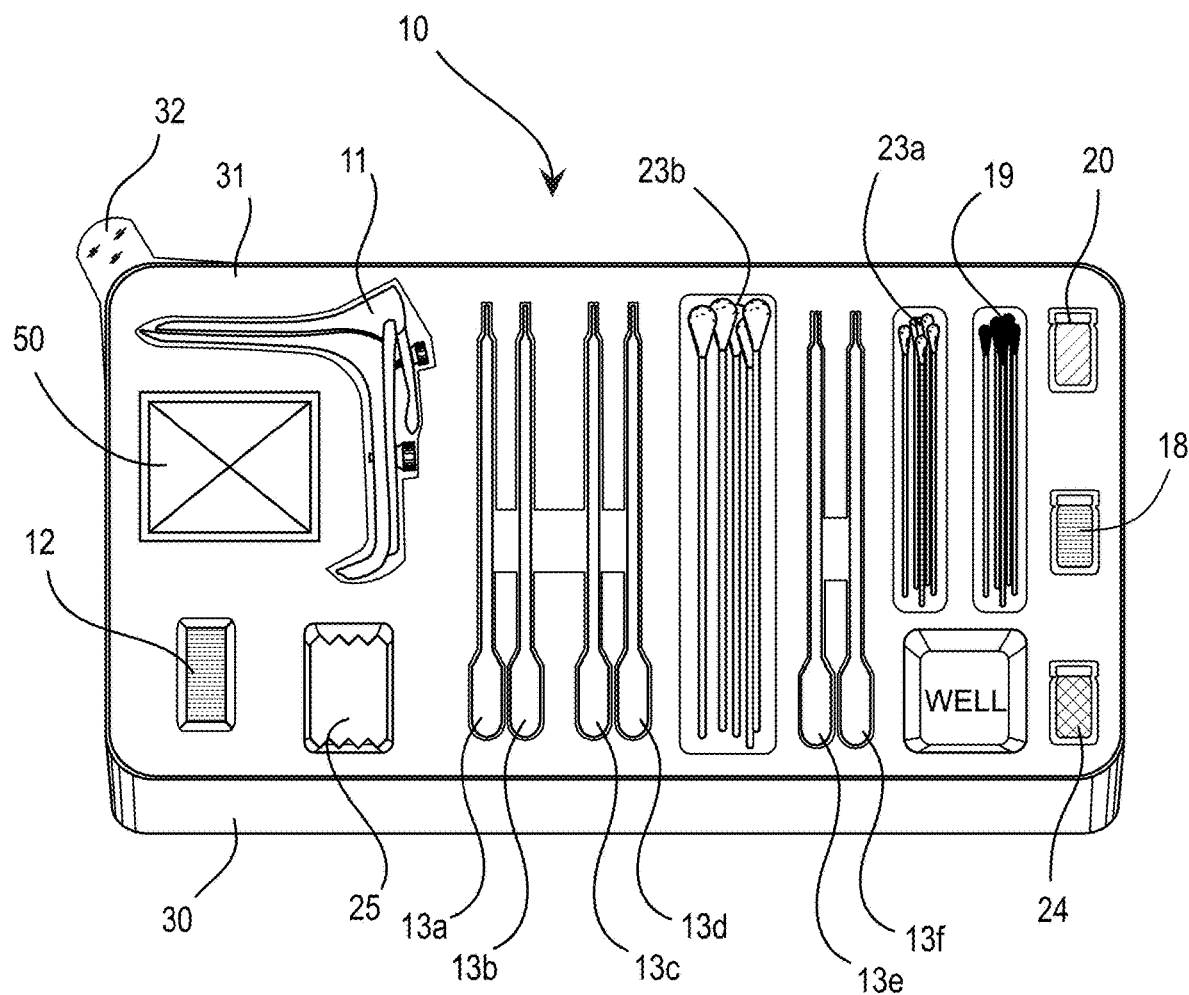
FIG. 1 shows a medical kit for diagnosing and treating neoplastic tissue in accordance with an embodiment.

The following embodiments are described in sufficient detail to enable one skilled in the art to make and use the invention. It is to be understood that other embodiments would be evident based on the present disclosure, and that system, process, mechanical, or chemical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known compositions, medical kit configurations, and process steps are not disclosed in detail.

The drawings showing embodiments of the medical kit are semi-diagrammatic and not to scale and, particularly, some of the dimensions are for the clarity of presentation and are shown exaggerated in the drawing figures.

Where multiple embodiments are disclosed and described having some features in common, for clarity and ease of illustration, description, and comprehension thereof, similar and like features one to another will ordinarily be described with similar reference numerals. The embodiments have been numbered first embodiment, second embodiment, etc. as a matter of descriptive convenience and are not intended to have any other significance or provide limitations for the present invention.

This disclosure relates to diagnosing neoplastic tissue as described in commonly owned U.S. patent application Ser. No. 14/870,642, filed Sep. 30, 2015, which claims benefit of priority with U.S. Prov. Ser. No. 62/057,584, filed Sep. 30, 2014; the entire contents of each of which are hereby incorporated by reference.

In addition, this disclosure relates to treating neoplastic tissue with trichloroacetic acid (TCA) as described in U.S. patent application Ser. No. 15/052,819, filed Feb. 24, 2016, which claims benefit of priority with U.S. Prov. Ser. No. 62/182,606, filed Jun. 21, 2015, and further claims benefit of priority with U.S. Prov. Ser. No. 62/120,356, filed Feb. 24, 2015; the contents of each of which are hereby incorporated by reference.

Now, it has been recently discovered that a medical kit which provides componentry for both diagnosis and treatment of neoplastic tissue is of particular need in the field, and a novel arrangement such a medical kit and methods for using the medical kit for concurrently performing a diagnosis and treatment of affected tissue is also of particular importance and demand in the field.

Turning now to FIG. 1, a medical kit 10 for use in the diagnosis and treatment of neoplastic tissue, such as, for example, tissue exhibiting cervical intraepithelial neoplasia (CIN), is illustrated.

As shown in the illustrated embodiment of FIG. 1, the medical kit 10 includes: a speculum 11; a light source 12; and a plurality of pre-filled containers 13(a-f), wherein the plurality of pre-filled containers comprises at least: a first containing normal saline solution 13a, a second containing acetic acid solution 13b, a third containing aqueous iodine (Lugol's) solution 13c, a fourth containing normal saline solution 13d, a fifth containing fluorescein sodium solution 13e, and a sixth containing normal saline solution 13f.

Each of these components may be provided in a tray 30, with a film cover 31 for sealing the components in a sterile environment. The film cover may comprise a pull tab 32. The tray may comprise one or more wells for mixing components related to the kit.

Shown in FIG. 1 are a plurality of small swabs 23a and large swabs 23b, such as cotton swabs or the like; gauze 25; silver nitrate sticks 19; trichloroacetic acid 18; basic ferric sulfate solution (Monsel's) 20; and an amber container 24. Other componentry 50 may be similarly provided (See FIG. 7).

The speculum can be an autoclavable metal speculum, or more preferably the speculum may comprise a disposable plastic speculum. The plastic speculum may comprise a transparent body configured to communicate light from the light source through the speculum and direct such light toward the cervix of the patient.

The light source 12 can be configurable in each of three states, including: (i) a first state wherein the light source in the first state is configured to emit polychromatic light for visualizing tissue, (ii) a second state wherein the light source in the second state is configured to emit green light for visualizing a pattern of vascularization in the tissue, and (iii) a third state wherein the light source in the third state is configured to emit blue light for visualizing staining of abnormal tissue.

The polychromatic light may comprise light in the spectral range of 350 nm to 700 nm.

The green light may consist essentially of light in the spectral range of 495 nm to 625 nm.

The blue light may consist essentially of light in the spectral range of 350 nm to 495 nm.

Figure 6:
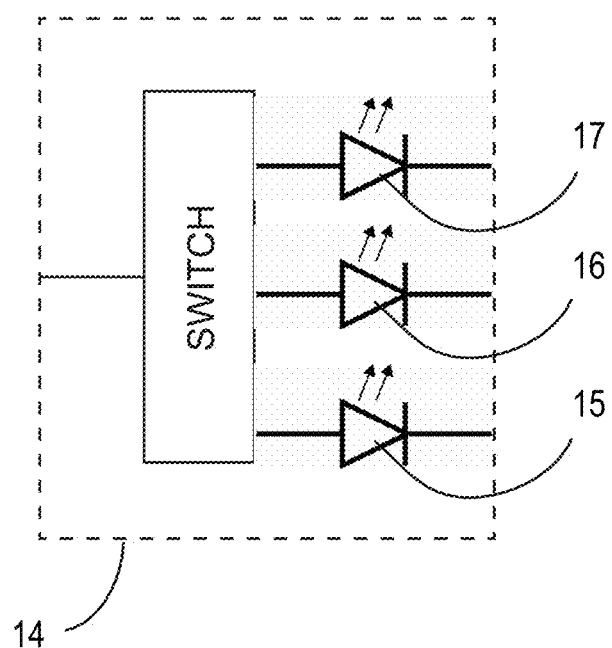
FIG. 6 shows a schematic electrical circuit including a switch and three light emitting diodes.

In some embodiments, the three states are each individually achieved via an electronic circuit (See FIG. 6) including a switch configured to selectively power one of three light emitting diodes, wherein each of the light emitting diodes 15; 16; 17, respectively, is configured to emit one of said polychromatic, green and blue lights. The light source powered by an electronic circuit is generally limited to the capacity of a battery coupled to the circuit. Once the battery power is exhausted, another battery may be replaced, or the light source may be discarded.

In other embodiments, the light source may comprise a chemiluminescent light source. Chemiluminescent lights are known by one with skill in the art, and generally include a container and two or more materials capable of causing a chemiluminescent reaction. In a chemiluminescent reaction, reactive intermediates are formed which enter electronically excited states. Subsequent transition back to ground state is accompanied by a release of energy in form of light. Such chemiluminescent light sources are useful for a limited duration and are used as a disposable light source.

The light source can be configured to couple with the speculum. IN this regard, the light source can be configured with a housing and a means for attaching the light source to the speculum, for example, by a clamp, clip, friction fitment, or other attachment means known to one having skill in the art.

Alternatively, the light source can be embodied within the speculum. Here, the light source is integrated on or within the speculum to provide an integrated light-emitting speculum.

The pre-filled containers may be configured in one of a myriad of possible implementations as would be appreciated by one with skill in the art. For example, the pre-filled containers may comprise pre-filled pipettes with twist-off caps.

The first 13a of the plurality of pre-filled containers containing normal saline solution may comprise a pre-filled pipette containing between 10.0 mL and 100.0 mL of the normal saline solution. For purposes herein, normal saline solution as generally used in medical procedures is acceptable for use in the various embodiments herein.

The second 13b of the plurality of pre-filled containers containing acetic acid may comprise a pre-filled pipette containing between 10.0 mL and 100.0 mL of 1%-10% acetic acid; or more preferably the pre-filled pipette may comprise 4% acetic acid solution.

The third 13c of the plurality of pre-filled containers may comprise a pre-filled pipette containing between 10.0 mL and 100.0 mL of aqueous iodine solution, said aqueous iodine solution comprising less than 2% concentration of iodine (Lugol's solution). In general, the Lugol's solution may comprise up to 5% iodine; however, less than 2% is preferred in order to mitigate the occurrence of potential complications and irritations.

The fourth 13d of the plurality of pre-filled containers containing normal saline solution may comprise a pre-filled pipette containing between 10.0 mL and 100.0 mL of the normal saline solution. Normal saline solution generally comprises 0.9% saline, though any commercially acceptable saline solution appreciated by one with skill in the art can be used.

The fifth 13e of the plurality of pre-filled containers containing fluorescein sodium solution (FNa) may comprise a pre-filled pipette containing between 10.0 mL and 100.0 mL of fluorescein sodium solution (FNa in aqueous solution). For example, the FNa may comprise 1.0 mg in 5 mL or 0.02% by weight. A much stronger concentration may be provided, for example, 1.0 g FNa in 5.0 mL solution or 2.0% by weight. FNa generally has less than 20% solubility in water, thus up to 20% FNa solution may be used.

Alternatively, the fifth of the plurality of pre-filled containers containing fluorescein sodium solution may comprise fluorescein sodium salt (solid phase FNa). In this regard, the FNa salt arrives in solid phase within the kit, but the FNa salt is generally mixed in solution prior to administering to the patient.

The sixth 13f of the plurality of pre-filled containers containing normal saline solution may comprise a pre-filled pipette containing between 10.0 mL and 100.0 mL of the normal saline solution.

The medical kit may further include trichloroacetic acid (TCA). The trichloroacetic acid may comprise 1.0% to 99.0% trichloroacetic acid in aqueous solution. In a preferred embodiment, the TCA comprises 85% concentration of trichloroacetic acid in aqueous solution.

The medical kit may further comprise one or more silver nitrate sticks. These silver nitrate sticks are conventionally available and used to coagulate tissue. Some silver nitrate sticks are mixed in composition, for example, may comprise about 75% silver nitrate and about 25% potassium nitrate. Any similar component for coagulating tissue that is known to one with skill in the art may be similarly implemented to achieve substantially similar results.

The medical kit may further comprise an amount of basic ferric sulfate solution (Monsel's solution). For example, 20% aqueous ferric subsulfate may be provided. Ferric subsulfate solution is a hemostatic agent used after superficial skin biopsies.

Figure 7:
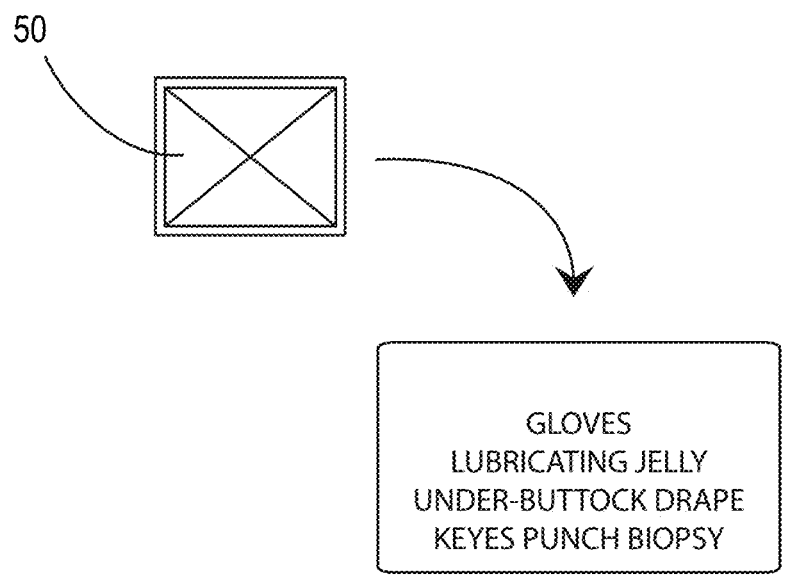
FIG. 7 shows the miscellaneous componentry of the medical kit, which may include: gloves, lubricating jelly, cotton swabs, one amber-colored glass jar, gauze, an under-buttock drape, a disposable Keyes biopsy punch or any combination of one or a plurality thereof.

As shown in FIG. 7, the medical kit may further comprise any number of other conventional medical procedure related components 50, such as for example: gloves, lubricating jelly, cotton swabs, one amber-colored glass jar, gauze, an under-buttock drape, a disposable Keyes biopsy punch or any combination of one or a plurality thereof.

In another aspect, a method for using the medical kit described herein for diagnosis and treatment of tissue exhibiting intraepithelial neoplasia (neoplastic tissue) is disclosed.

In a preferred embodiment, as shown in FIG. 2, the method includes at least: providing a medical kit comprising: a speculum, a light source, and a plurality of pre-filled containers, wherein the plurality of pre-filled containers comprises at least: a first containing normal saline solution, a second containing acetic acid, a third containing Lugol's aqueous iodine solution, a fourth containing normal saline solution, a fifth containing fluorescein sodium solution and a sixth containing normal saline solution; diagnosing the cervical intraepithelial neoplasia, and treating the cervical tissue indicating intraepithelial neoplasia.

In a preferred embodiment, as shown in FIG. 3, the diagnosing step may comprise: inserting the speculum into a patient's vagina to expose the entire cervix of the patient; rinsing the patient's cervix with the normal saline solution contained in the first of the pre-filled containers to remove discharge and detritus; using the light source and colposcope: visually identifying abnormal cervical vasculature with green light from the light source; applying the acetic acid contained in the second of the pre-filled containers to the patient's cervix for staining abnormal tissue acetowhite; applying aqueous iodine solution contained in the third of the pre-filled containers to the patient's cervix for staining normal tissue brown; using the colposcope: visualizing the patient's cervix and identifying brown staining of benign tissue in conjunction with acetowhite staining of abnormal tissue, and recording findings; rinsing the patient's cervix with the normal saline solution contained in the fourth pre-filed containers; applying the fluorescein sodium solution contained in the fifth of the pre-filled containers to the patient's cervix; visualizing fluorescent green staining of malignant and premalignant tissue using blue light of the light source, and recording findings; rinsing the patient's cervix with the normal saline solution contained in the sixth of the pre-filled containers; performing one or more cervical biopsies and endocervical curettage if desired to compare with cytological results or proceeding with treatment based on the findings; and if biopsies are performed and bleeding occurs at biopsy sites, obtaining hemostasis by applying silver nitrate to affected areas.

Figure 4:
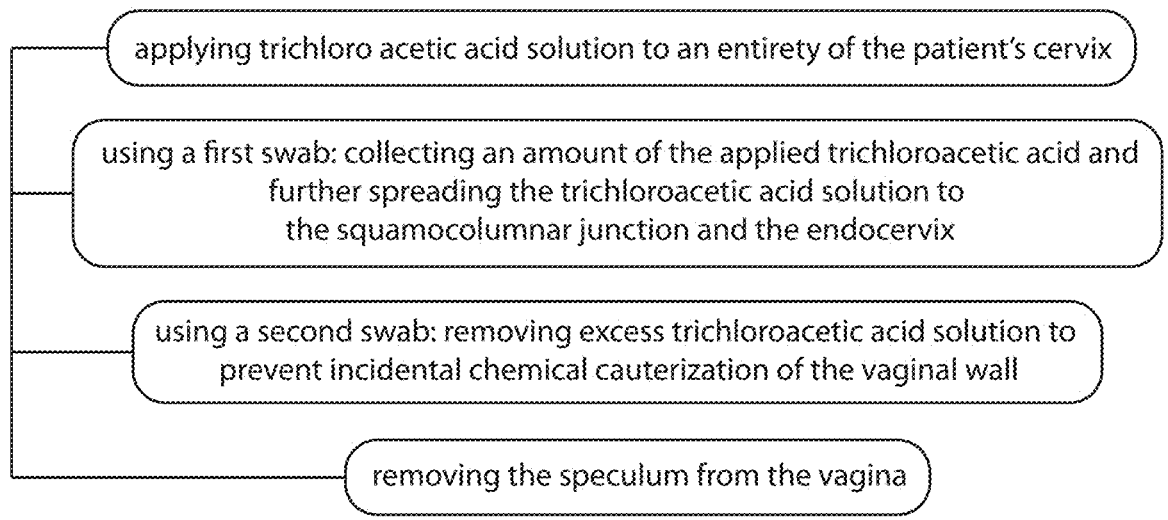
FIG. 4 further illustrates additional steps for treating neoplastic tissue using the medical kit as-illustrated in FIG. 1.

In another preferred embodiment, as shown in FIG. 4, the treating step may comprise: applying trichloro acetic acid solution to an entirety of the patient's cervix; using a first swab: collecting an amount of the applied trichloroacetic acid and further spreading the trichloroacetic acid solution to the squamocolumnar junction and the endocervix; using a second swab: removing excess trichloroacetic acid solution to prevent incidental chemical cauterization of the vaginal wall; removing the speculum from the vagina; and repeating the diagnosing and treating until there are no findings of neoplastic tissue.

Figure 5:
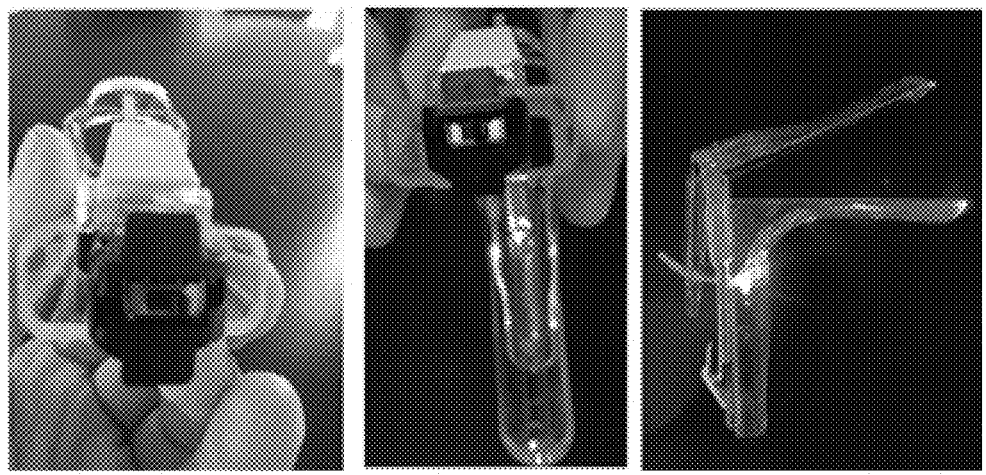
FIG. 5 shows a speculum with a light source embedded therein.

FIG. 5 shows a lighted speculum. Here, the light source is configured to couple with the speculum, the light source comprises an electronic circuit (See FIG. 6) capable of selectively configuring the light source in one of three states as described above, wherein the light source is configured to emit one of the polychromatic, green, or blue lights when configured in each of the three states. Also shown, the speculum can act as a medium for communicating light to the treatment site of the patient.

Figure 8:
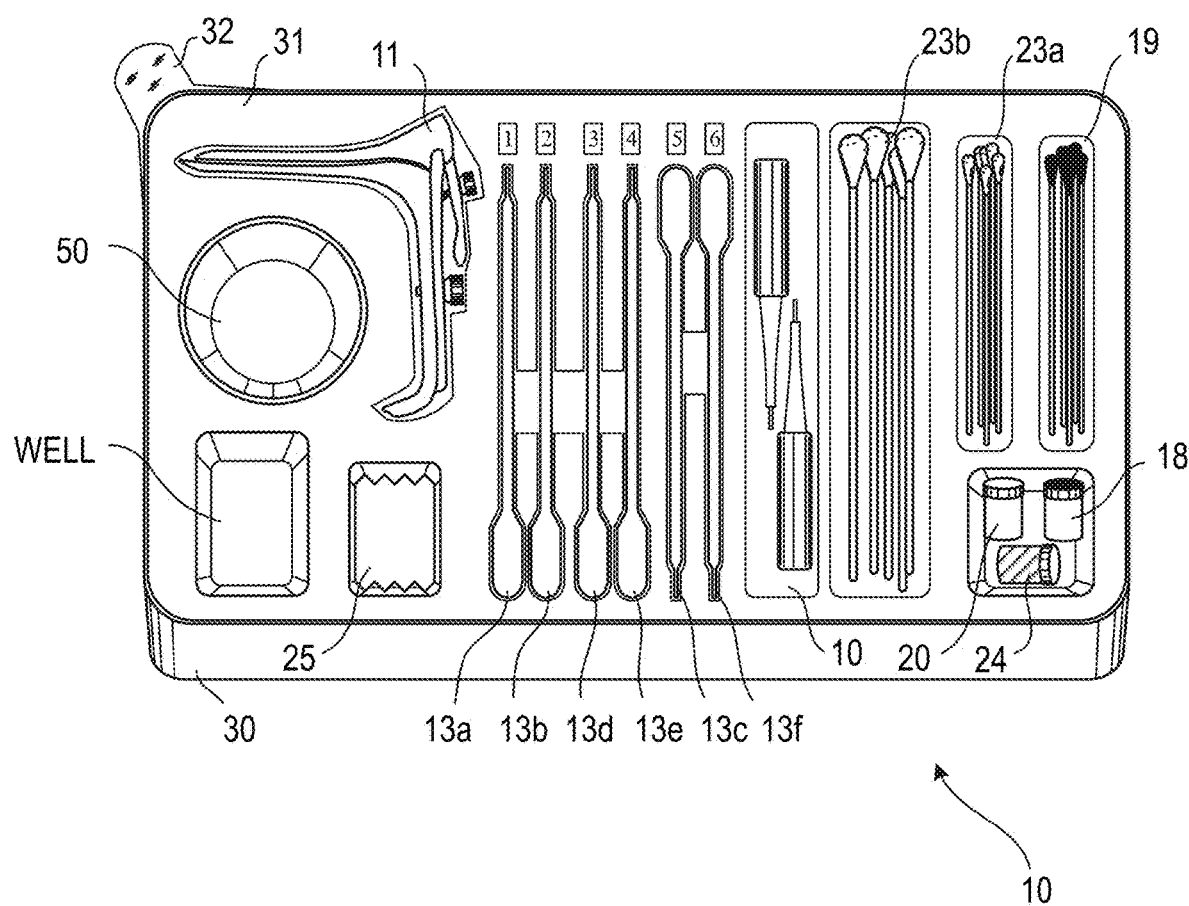
FIG. 8 shows a medical kit for diagnosing and treating neoplastic tissue in accordance with another embodiment.

FIG. 8 shows a medical kit for diagnosing and treating neoplastic tissue in accordance with another embodiment. Here, the speculum comprises a light source built-in or embedded into the speculum unit. In this embodiment, the speculum is preferably a disposable lighted speculum.

It is further contemplated that while a colposcope may be the preferred conventional instrument for visualizing stained tissue, other systems may be similarly utilized. For example, a laptop computer, tablet or even cell phone (smart phone) can be used as a "computer" and coupled to a camera (or use a camera thereof) for taking pictures and/or video of the treatment site. Thus, a colposcope is not explicitly required and the invention can be practiced with other electronic means, such as with a cell phone, tablet PC, laptop or similar device.

Each of the above-described components of the medical kit may be substituted for other elements as described in the incorporated parent applications, which disclosure is incorporated by reference.

Other variations of the instant disclosed features and embodiments, particularly when combined with other features and methods known in the art, are deemed to be included within the spirit and scope of this disclosure.

FEATURES LIST medical kit 10
a speculum 11
a light source 12
pre-filled containers 13
first pre-filled container containing saline solution 13a
second pre-filled container containing acetic acid 13b
third pre-filled container containing fluorescein sodium 13c
pre-filled pipette containing aqueous iodine solution 13d
other pre-filled pipettes containing saline solution 13e; 13f
electronic circuit 14
polychromatic light emitting diode 15
green light emitting diodes 16
blue light emitting diodes 17
trichloroacetic acid 18 silver nitrate sticks 19
basic ferric sulfate solution 20
gloves 21
lubricating jelly 22
cotton swab 23
an amber-colored glass jar 24
gauze 25
under-buttock drape 26
tray 30
film 31
film tab 32
componentry 50

What is claimed is:

1. A medical kit for use in the diagnosis and treatment of tissue exhibiting intraepithelial neoplasia, the medical kit comprising:
    a speculum;
    a light source;
    a first pre-filled container containing saline solution;
    a second pre-filled container containing acetic acid; and
    a third pre-filled container containing fluorescein sodium.

2. The medical kit of claim 1, wherein the light source is configurable in a first state, a second state, and a third state,
    wherein the light source in the first state is configured to emit polychromatic light for visualizing tissue,
    wherein the light source in the second state is configured to emit green light for visualizing a pattern of vascularization in the tissue, and
    wherein the light source in the third state is configured to emit blue light for visualizing staining of abnormal tissue.

3. The medical kit of claim 2, wherein said polychromatic light comprises light in the spectral range of 350 nm to 700 nm.

4. The medical kit of claim 2, wherein said green light consists essentially of light in the spectral range of 495 nm to 625 nm.

5. The medical kit of claim 2, wherein said blue light consists essentially of light in the spectral range of 350 nm to 495 nm.

6. The medical kit of claim 2, further comprising an electronic circuit configured to selectively power one of three light emitting diodes, wherein each of the light emitting diodes is configured to emit one of said polychromatic, green and blue lights corresponding to the first state, the second state, and the third state, respectively.

7. The medical kit of claim 1, wherein the light source is configured to couple with the speculum.

8. The medical kit of claim 1, wherein the light source is embodied within the speculum.

9. The medical kit of claim 1, wherein the first pre-filled container comprises a pre-filled pipette containing between 10.0 mL and 100.0 mL of the saline solution.

10. The medical kit of claim 9, wherein the second pre-filled container comprises a pre-filled pipette containing between 10.0 mL and 100.0 mL of 4% acetic acid solution.

11. The medical kit of claim 10, wherein the third pre-filled container comprises a pre-filled pipette containing between 10.0 mL and 100.0 mL of fluorescein sodium solution.

12. The medical kit of claim 10, wherein the third pre-filled container containing fluorescein sodium comprises fluorescein sodium salt.

13. The medical kit of claim 1, further comprising a fourth pre-filled pipette containing between 10.0 mL and 100.0 mL of aqueous iodine solution, the aqueous iodine solution comprising more than 2% concentration of iodine and less than 5% concentration of iodine.

14. The medical kit of claim 1, further comprising trichloroacetic acid.

15. The medical kit of claim 14, wherein the trichloroacetic acid comprises 1.0% to 99.0% trichloroacetic acid in aqueous solution.

16. The medical kit of claim 1, further comprising one or more silver nitrate sticks.

17. The medical kit of claim 1, further comprising an amount of basic ferric sulfate solution.

18. The medical kit of claim 1, further comprising at least one of gloves, lubricating jelly, a cotton swab, an amber-colored glass jar, gauze, and an under-buttock drape.

19. The medical kit of claim 1, wherein the light source comprises a chemiluminescent light source.

20. The medical kit of claim 1, further comprising a biopsy device.

21. A method for practicing the diagnosis and treatment of tissue exhibiting intraepithelial neoplasia, the method comprising:
    providing a medical kit comprising: a speculum, a light source, a first pre-filled container containing saline solution, a second pre-filled container containing acetic acid, and a third pre-filled container containing fluorescein sodium;
    diagnosing the cervical intraepithelial neoplasia, the diagnosing comprising:
        inserting the speculum into a patient's vagina to expose the entire cervix of the patient;
        rinsing the patient's cervix with the saline solution contained in the first pre-filled container to remove discharge and detritus;
        visually identifying, using the light source and a colposcope, abnormal cervical vasculature with green light from the light source;
        applying the acetic acid contained in the second pre-filled container to the patient's cervix for staining abnormal tissue acetowhite;
        applying aqueous iodine solution to the patient's cervix for staining normal tissue brown;
        visualizing, using the colposcope, the patient's cervix and identifying brown staining of benign tissue in conjunction with acetowhite staining of abnormal tissue, and recording findings;
        rinsing the patient's cervix with the saline solution;
        applying the fluorescein sodium contained in the third pre-filled container to the patient's cervix;
        visualizing fluorescent green staining of malignant and premalignant tissue using blue light of the light source, and recording findings;
        rinsing the patient's cervix with the saline solution;
        performing one or more cervical biopsies and/or endocervical curettage to compare with cytological results; and
        if biopsies are performed and bleeding occurs at biopsy sites, obtaining hemostasis by applying silver nitrate to affected areas; and
    treating the cervical tissue indicating intraepithelial neoplasia based on a finding of the diagnosing, the treating comprising:
        applying trichloroacetic acid solution to an entirety of the patient's cervix;
        collecting, using a first swab, an amount of the applied trichloroacetic acid and further spreading the trichloroacetic acid solution to a squamocolumnar junction and an endocervix;

removing, using a second swab, excess trichloroacetic acid solution to prevent incidental chemical cauterization of the vaginal wall;
removing the speculum from the vagina; and
repeating the diagnosing and treating until there are no findings of neoplastic tissue.

* * * * *